(12) United States Patent
Maidhof et al.

(10) Patent No.: US 8,946,487 B2
(45) Date of Patent: Feb. 3, 2015

(54) PROCESS FOR PREPARING DIVINYL ETHERS

(75) Inventors: Thomas Maidhof, Ockenheim (DE); Helmut Kronemayer, Heidelberg (DE); Georg Heinrich Grosch, Bad Dürkheim (DE); Regina Vogelsang, Ludwigshafen (DE); Klaus Peter Gumbel, Mannheim (DE); Tim Balensiefer, Mannheim (DE); Alexey Shilkin, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 434 days.

(21) Appl. No.: 13/398,257

(22) Filed: Feb. 16, 2012

(65) Prior Publication Data
US 2012/0215033 A1 Aug. 23, 2012

Related U.S. Application Data

(60) Provisional application No. 61/443,728, filed on Feb. 17, 2011.

(51) Int. Cl.
   *C07C 41/08* (2006.01)
   *C07C 41/42* (2006.01)
   *C07C 43/16* (2006.01)

(52) U.S. Cl.
   CPC .............. *C07C 41/08* (2013.01); *C07C 41/42* (2013.01)
   USPC .......................................... 568/688; 568/616

(58) Field of Classification Search
   CPC .......... C07C 41/08; C07C 41/42; C07C 41/46
   USPC ................................................ 568/688, 616
   See application file for complete search history.

(56) References Cited

U.S. PATENT DOCUMENTS

| | | | | |
|---|---|---|---|---|
| 1,959,927 A | * | 5/1934 | Reppe | 564/508 |
| 2,527,853 A | * | 10/1950 | Roach et al. | 568/670 |
| 3,287,420 A | * | 11/1966 | Johnson, Jr. et al. | 568/675 |
| 3,657,360 A | * | 4/1972 | Carluccio et al. | 568/675 |
| 5,674,949 A | * | 10/1997 | Bierschenk et al. | 525/331.6 |
| 6,093,855 A | * | 7/2000 | Lorenz | 568/621 |

FOREIGN PATENT DOCUMENTS

| | | | | |
|---|---|---|---|---|
| EP | 0 733 401 A2 | | 9/1996 | |
| EP | 0 906 899 A1 | | 4/1999 | |
| JP | 10-045653 | * | 2/1998 | C07C 43/15 |
| JP | 10-182536 | * | 7/1998 | C07C 43/16 |
| JP | 2006-008519 | * | 1/2006 | C07C 41/42 |

OTHER PUBLICATIONS

International Search Report issued May 29, 2012 in PCT/EP2012/052369 filed Feb. 13, 2012 with English Translation of Category of Cited Documents.
M. F. Shostakovskii, et al., "Vinyl Ethers of Di- and Tri-Ethylene Glycols", Journal of General Chemistry of the USSR, vol. 34, No. 7, XP009159135, Jul. 1, 1964, pp. 2125-2128 plus cover page.
"Ullmann's Encyclopedia of Industrial Chemistry", Sixth, Completely Revised Edition, vol. 38, (Vanadium and Vanadium Compounds to Wastewater), "Vinyl Ethers", 2003, 11 pages.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

Process for preparing divinyl ethers by reacting compounds having two hydroxyl groups (hereinafter referred to as diols) with acetylene, wherein
   the hydroxyl groups are incompletely reacted with acetylene and the resulting product mixture therefore comprises the monovinyl ether in addition to the divinyl ether and
   the monovinyl ether is separated off from the product mixture by extractive distillation in the presence of an extractant.

17 Claims, No Drawings

PROCESS FOR PREPARING DIVINYL ETHERS

The present application incorporates the provisional U.S. application 61/443,728 filed on Feb. 17, 2011 by reference.

The invention relates to a process for preparing divinyl ethers by reacting compounds having two hydroxyl groups (hereinafter referred to as diols) with acetylene, wherein the hydroxyl groups are incompletely reacted with acetylene and the resulting product mixture therefore comprises the monovinyl ether in addition to the divinyl ether and the monovinyl ether is separated off from the product mixture by extractive distillation in the presence of an extractant.

Vinyl ethers, also known as divinyl ethers, can be prepared by the Reppe process. A comprehensive description of this process may be found in Ullmann's Encyclopedia of Industrial Chemistry, Vol. 38, pages 77 to 85. The essential feature of this process is the reaction of hydroxy compounds with acetylene to form the corresponding vinyl ethers. The reaction is generally carried out in the presence of an alkali metal base, e.g. the alkoxide of the hydroxy compounds, which is formed by addition of alkali metal hydroxide to the hydroxy compound.

In the case of compounds having two hydroxy groups (diols), the monovinyl ether of the diol is generally formed first; only then does further acetylene react with the second hydroxy group to give the divinyl ether. Long reaction times are required for complete reaction to the divinyl ether since the reaction probability becomes ever lower with increasing number of hydroxy groups still present. The reaction is also associated with a viscosity increase which makes complete reaction to the divinyl ether more difficult. The problem of the viscosity increase occurs particularly in the reaction of the diol with acetylene in the absence of a contiguous gas phase. Such a reaction with acetylene is known from EP-A 733401. Here, the reactor is completely filled and the gaseous acetylene is introduced into the liquid phase so that it becomes distributed in the liquid phase without a contiguous gas phase comprising acetylene being formed. In the case of a batch process, the contents of the reactor are depressurized into an equalization vessel and the reaction mixture is returned to the reactor. In a continuous process, the contents of the reactor are likewise depressurized into an equalization vessel, but are not returned to the reactor but are instead fed continuously to the downstream work-up. These methods of carrying out the process are made particularly difficult by high viscosities of the reaction mixture.

Therefore, interrupting the reaction before complete conversion to the divinyl ether has been achieved is known from EP-A 906 899. A monovinyl ether is separated off by distillation from the resulting product mixture after addition of a metal hydroxide. A disadvantage of this process is that the addition of metal hydroxide is only industrially feasible and practical at monovinyl ether contents of 0-3%. At monovinyl ether contents greater than 3%, the monovinyl ether metal salts lead to high viscosities and blockages in the bottom of the columns.

It was an object of the present invention to provide a very simple process for preparing divinyl ethers in high purity and yield which can be carried out continuously. In particular, a process in which no additional starting materials are required is desired.

We have accordingly found the process defined at the outset.

In the process of the invention, compounds having two hydroxyl groups (diols) are reacted with acetylene.

The diols are preferably aliphatic or cycloaliphatic compounds having a molecular weight of less than 500 g/mol, in particular less than 300 g/mol. The diols preferably do not contain any further functional groups or heteroatoms apart from the two hydroxyl groups.

Preferred diols are those of the formula I

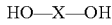

HO—X—OH or the formula II

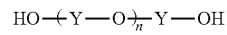

HO—(Y—O)$_n$—Y—OH where X and Y are each a C2-C10-alkylene group and n is an integer from 1 to 10.

X in formula I is particularly preferably a C2-C6-alkylene group. Particularly preferred compounds of the formula I are 1,2-dihydroxyethane (ethylene glycol), 1,3-dihydroxypropane, 1,4-dihydroxybutane and 1,6-dihydroxyhexane.

Y in formula II is particularly preferably a C2-C4-alkylene group. n is particularly preferably an integer from 1 to 6, in particular 1, 2, 3 or 4.

In a particularly preferred embodiment, Y is an ethylene group and n is an integer from 1 to 4.

As particularly preferred diols for the process of the invention, mention may be made of the compounds diethylene glycol (n=1) and triethylene glycol (n=2) of the formula II.

It is also possible to use mixture of diols, and the statements made below therefore also apply to mixtures; however, preference is given to pure diols which can, however, comprise normal industrial impurities.

The reaction of the diol with acetylene is preferably carried out in the presence of a catalyst. The alkali metal alkoxide of the diol is preferably used as catalyst. For this purpose, the diol is partly converted by addition of sodium hydroxide or potassium hydroxide in solid or aqueous form into the corresponding sodium or potassium alkoxide before the reaction with acetylene. Preference is given to converting from 0.1 to 20 mol %, in particular from 0.5 to 10 mol %, of the hydroxy groups into alkoxide groups and selecting the amount of alkali metal hydroxide correspondingly.

The above reaction of the diol with alkali metal hydroxide can be carried out batchwise or continuously. The mixture is preferably dewatered during the reaction. A batch reaction is preferably carried out under reduced pressure and temperatures of up to 200° C., in particular at from 1 to 100 mbar and from 140 to 180° C. A continuous reaction with the alkali metal hydroxide can be carried out as a reactive distillation with removal of the water by distillation.

The reaction with acetylene is preferably carried out using a diol having the above-mentioned content of alkoxide groups and a water content of less than 1% by weight, in particular less than 0.5% by weight.

The reaction of the acetylene with the diol is preferably carried out at temperatures of from 80 to 220° C., particularly preferably from 140 to 180° C., and preferably at pressures of from 1.0 (atmospheric pressure) to 50 bar and particularly preferably from 5 to 30 bar.

The reaction can be carried out in any reactors; mention may be made by way of example of stirred vessels, cascades of stirred vessels, tube reactors or loop reactors. The reaction is preferably carried out in a loop reactor.

In particular, the reaction is carried out with avoidance of a contiguous gas phase comprising acetylene, as is also described in EP-A 733401. For this purpose, the reaction vessel is preferably completely filled with the diol and acetylene is introduced into the liquid phase to the desired degree of saturation. An output stream is preferably depressurized into an equalization vessel and returned to the reactor so as to determine the composition and acetylene concentration of the reaction mixture. However, the invention is also particularly suitable for a continuous reaction. In a continuous reaction, the contents of the reactor after depressurization into an equalization vessel are preferably not returned to the reactor but instead are fed continuously to the downstream work-up.

According to the invention, complete conversion into the divinyl ether does not occur. The reaction is carried out only to such an extent that the desired amount of monovinyl ether is still comprised in the product mixture. The product mixture preferably comprises
from 30 to 98% by weight of divinyl ether and
from 2 to 70% by weight of monovinyl ether,
based on the total weight of divinyl ether and monovinyl ether.

The product mixture particularly preferably comprises
from 60 to 95% by weight of divinyl ether and
from 5 to 40% by weight of monovinyl ether,
based on the total weight of divinyl ether and monovinyl ether.

Furthermore, the product mixture can also comprise unreacted diol in which none of the hydroxy groups have been converted into vinyl ether groups, e.g. in amounts of from 0 to 40 parts by weight, in particular from 0.5 to 30 parts by weight, per 100 parts by weight of the total weight of divinyl ether and monovinyl ether. In addition, the product mixture comprises basic salts of the alkali metals as by-products or as unreacted starting materials.

In a subsequent work-up of the product mixture, the basic salts of the alkali metals can firstly be separated. This can, for example, be carried out in a thin film evaporator through which the entire product mixture or only a substream of the product mixture is conveyed.

An important feature of the process of the invention is the removal of the monovinyl ether from the product mixture by means of an extractive distillation.

The extractive distillation can follow a prior work-up, e.g. the preceding salt removal.

It is an advantage of the process of the invention that the product mixture directly from the reaction without further work-up or without prior removal of by-products, catalysts (salt removal) or unreacted starting materials can be used for the extractive distillation of the product mixture.

The product mixture is therefore preferably fed directly from the reactor to the extractive distillation.

Suitable extractants are organic solvents in which the monovinyl ether is sufficiently soluble. Possibilities are, in particular, aliphatic and cycloaliphatic compounds having a molecular weight below 200 g/mol. Aliphatic or cycloaliphatic compounds having at least one hydroxy group or carbonyl group are particularly useful.

The above diols of the formula I and formula II are particularly suitable as extractant.

In a particularly preferred embodiment, the diols used in the reaction with acetylene are also used as extractant in order to separate monovinyl ethers of these diols from the product mixture.

Accordingly, diethylene glycol

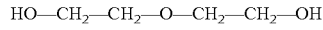

is preferably used as extractant in the preparation of diethylene glycol divinyl ether

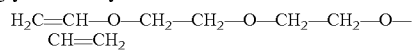

and triethylene glycol

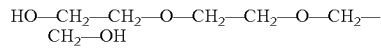

is preferably used as extractant in the preparation of triethylene glycol divinyl ether

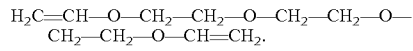

The extractant is preferably used in an amount of from 5 to 100 parts by weight, particularly preferably from 20 to 80 parts by weight, in particular from 30 to 60 parts by weight, per 100 parts by weight of the total weight of monovinyl and divinyl ethers. In a continuous process, these parts by weight correspond to the weight ratio of the streams fed in.

The extractive distillation is, in particular, carried out at from 60 to 240° C. and at a reduced pressure of from 0.001 to 1 bar. For example, at a reduced pressure of from 1 to 50 mbar, a suitable temperature at the bottom is from 130 to 190° C. and a suitable temperature at the top is from 80 to 120° C.

At the bottom of the column, a mixture enriched in the monovinyl ether is obtained (bottom mixture).

Above the bottom, a mixture enriched in the desired divinyl ether (product mixture) can be taken off at a suitable point.

The monovinyl ether can be separated off from the bottom mixture and returned to the reaction with acetylene. When the diol used in the reaction is at the same time also the extractant (see preferred embodiments above), a work-up of the bottom mixture enriched in monovinyl ether can be dispensed with and the total bottom mixture can be recirculated without work-up, either to the reaction with the alkali metal hydroxide (see above) or directly to the reaction with the acetylene; in this case, the amount of extractant (that is to say of the corresponding diol) is preferably selected according to its nature so that the volume of the bottom mixture obtained does not exceed the volume available of the reactor into which it is recirculated; the amount of extractant is particularly preferably selected so that the volume of the bottom mixture obtained and recirculated corresponds to the available volume of the reactor into which it is recirculated and fully exploits this volume.

Depending on the configuration of the apparatus, in particular the number of plates, the extractive distillation can directly give a product mixture which comprises the divinyl ether in the desired purity. As an alternative, when the apparatus is designed in a less demanding way, a product mixture which is enriched in the divinyl ether but still comprises diol and optionally reduced amounts of monovinyl ether can be taken off. This product mixture can then be fractionated further by distillation so as to give the divinyl ether in the desired purity. The diol obtained and any residual monovinyl ether can once again be recirculated without work-up as described above when the extractant is identical to the diol used in the reaction.

Suitable columns for the extractive distillation are columns comprising random packing elements or ordered packing, and these are, in particular, operated continuously.

Columns which comprise both random packing elements and ordered packing, e.g. beds of random packing in the lower part and ordered packing elements (e.g. built-in steel sheets) in the upper part, are suitable.

The columns can preferably have at least two, particularly preferably at least 3, theoretical plates. The number of theoretical plates can be, for example, from 2 to 100, in particular from 3 to 20.

An extractive distillation can, for example, give a bottom mixture comprising
from 10 to 70% by weight, in particular from 15 to 50% by weight, of monovinyl ether, and particularly preferably from 20 to 40% by weight of monovinyl ether,
from 2 to 50% by weight, in particular from 2 to 40% by weight, of divinyl ether, and particularly preferably from 5 to 30% by weight of divinyl ether,
from 10 to 90% by weight, in particular from 30 to 90% by weight, of diol and particularly preferably from 40 to 80% by weight of diol and
from 0 to 20% by weight, in particular from 0 to 10% by weight, of other constituents,
and a product mixture comprising
from 0 to 15% by weight, in particular from 0 to 5% by weight, of monovinyl ether, particularly preferably from 0 to 2% by weight of monovinyl ether,
from 60 to 99.5% by weight, in particular from 80 to 99.5% by weight, of divinyl ether, particularly preferably from 90 to 99.5 of divinyl ether
from 0.2 to 20% by weight, in particular from 0.2 to 10% by weight, of diol and particularly preferably from 0.2 to 5% by weight of diol and
from 0 to 10% by weight, in particular from 0 to 5% by weight, of other constituents.

The divinyl ether can easily be separated off from the product mixed by distillation in a purity of greater than 99% by weight, in particular greater than 99.5% by weight, with the amount of diol in the divinyl ether preferably being less than 0.5% by weight and in particular less than 0.2% by weight. Given an appropriate design of the apparatus, the divinyl ether can also be obtained directly from the extractive distillation in the same purity.

The process of the invention can be carried out batchwise or continuously. It is also possible, if the apparatus is designed appropriately, for process steps carried out continuously to be combined with steps carried out batchwise. In a preferred embodiment, the process is carried out continuously in all process steps.

The process of the invention is suitable both for batch operation and for continuous operation. It is technically simple to carry out. The process makes it possible to obtain divinyl ethers in high yield and purity. Viscosity increases as occur at high conversions to divinyl ethers and lead to problems can be avoided.

EXAMPLE

Synthesis of Diethylene Glycol Divinyl Ether

Diethylene glycol reacts with acetylene using KOH as base (formation of the alkoxide) to form the divinyl ether or a mixture of divinyl ether and monovinyl ether (in the case of partial conversion) according to the following reaction equation:

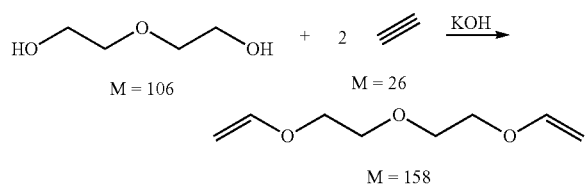

Abbreviations diethylene glycol: DEG
diethylene glycol monovinyl ether: DEG-MVE
diethylene glycol divinyl ether: DEG-DVE 1. Preparation of the Mixture of Monovinyl and Divinyl Ether Glycol
batch: 1720 g of diethylene glycol=16.2 mol
280 g of diethylene glycol divinyl ether=1.8 mol
50.0 g of KOH pellets The components were introduced into a 2.5 liter autoclave. Acetylene was introduced into the autoclave until the pressure was 19 bar. The reaction was carried out at 155° C., 19 bar and a stirrer speed of 700 rpm. After 550 liters of acetylene had been taken up (after about 7 hours), the reaction was interrupted, the autoclave was depressurized and cooled to room temperature.

A mixture of monovinyl and divinyl ethers of ethylene glycol was obtained. Gas-chromatographic analysis indicated a ratio of DEG-DVE to DEG-MVE of 68:29 (percent by area).

2. Salt Removal

A crude product obtained from a reaction of DEG with acetylene (comprising about 19% by weight of DEG-MVE) is continuously freed of the basic salts by means of a thin film evaporator at a heat transfer medium temperature in the evaporator of 110° C. and a pressure of 10 mbar abs. at a throughput of about 300 ml/h and with addition of about 10% of inert bottoms diluent (Pluriol® E600). The distillate obtained comprises about 14% by weight of DEG-MVE.

3. Extractive Distillation

At a feed stream flow of about 300 g/h, the crude distillate (comprising 14% of DEG-MVE) was fed to the bottom section of an appropriately dimensioned distillation column having top, bottom and side offtake and structured packing (Sulzer DX, packing height about 0.95 m). A reflux ratio of 20:1 at the top and 1:1 at the side offtake is set.

The temperature at the bottom was 105° C.

At a reduced pressure of about 20 mbar, a temperature of about 74° C. is established at the top.

At the same time, a stream of about 140 g/h of DEG was fed in as extractant at the level of the side offtake, as a result of which enrichment of DEG-MVE is achieved in the bottom of the column (about 30% of DEG-MVE, 60% of DEG and 10% of DEG-DVE).

The stream from the bottom of the column (about 204 g/h) can then be taken off and returned to the preparation of the base or to the reaction.

At the side offtake for liquid on the column, about 216 g/h were taken off (composition: about 0.1% of DEG-MVE, 1% of DEG and 99% of DEG-DVE) and fed to the pure distillation.

At the top of the column, about 15 g/h of low boilers are taken off.

4. Pure Distillation (Batch/Continuous)

The stream from the side offtake of the extractive distillation now has to be freed of DEG in the pure distillation. For this purpose, it is fed at about 221 g/h into the bottom of a further distillation column (simple top/bottom separation without side offtake) having structured packing.

The temperature at the bottom should be about 112° C.

At a reduced pressure of about 20 mbar, a temperature of about 85° C. is established at the top.

A reflux ratio of 3:1 is set at the top of the column.

At the top of the column, about 209 g/h of desired product having a purity of not less than 99% (and about 0.1% of DEG) are taken off.

A stream of about 12 g/h is taken off from the bottom of the column and can be returned to the preparation of the base or to the reaction.

5. Recirculation of the Bottoms from the Extractive Distillation and Renewed Reaction 1596 g of bottoms from the reactive distillation were reacted again with acetylene. The bottoms had the following composition:

| | | |
|---|---|---|
| 3.9% | of diethylene glycol divinyl ether | |
| 50.6% | of diethylene glycol monovinyl ether | (6.1 mol) |
| 43.5% | of diethylene glycol | (6.5 mol) |

Potassium content according to analysis (elemental analysis): 1.5%

The reaction was again carried out in a 2.5 liter autoclave as described above.

Gas-chromatographic analysis indicated 94.5 percent by area of DEG-DVE. A content of DEG-MVE could no longer be determined.

The invention claimed is:

1. A process for preparing a divinyl ether, comprising:
reacting a diol having two hydroxyl groups with acetylene, wherein the hydroxyl groups are incompletely reacted with acetylene and a resulting product mixture comprises monovinyl ether and divinyl ether; and
separating off the monovinyl ether from the product mixture by extractive distillation in the presence of an extractant,
wherein the product mixture comprises from 60 to 95% by weight of divinyl ether and from 5 to 40% by weight of monovinyl ether, based on a total weight of divinyl ether and monovinyl ether, and the extractant is the diol.

2. The process according to claim 1, wherein the diol is an aliphatic or cycloaliphatic compound having a molecular weight of less than 500 g/mol.

3. The process according to claim 1, wherein the diol is an aliphatic diol of formula I:

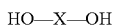  (I)

or formula II:

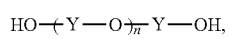  (II)

wherein X and Y are each independently a C2-C10-alkylene group and n is an integer of from 1 to 10.

4. The process according to claim 1, wherein the diol is diethylene glycol or triethylene glycol.

5. The process according to claim 1, wherein the reaction of the diol with acetylene is carried out in the absence of a contiguous gas phase.

6. The process according to claim 1, wherein the entire product mixture is fed to the extractive distillation without a prior removal of by-products, catalysts or unreacted starting materials.

7. The process according to claim 1, wherein an amount of the extractant is from 5 to 100 parts by weight per 100 parts by weight of monovinyl and divinyl ethers.

8. The process according to claim 1, wherein the extraction is carried out at a temperature of from 60 to 240° C. and a pressure of from 0.001 to 1 bar.

9. The process according to claim 1, further comprising returning the monovinyl ether separated off in the extractive distillation to the reaction.

10. The process according to claim 1, wherein the monovinyl ether which has been separated off is returned in a mixture with diol to the reaction.

11. The process according to claim 1, wherein the process is a continuous process.

12. The process according to claim 3, wherein the diol is an aliphatic diol of formula I.

13. The process according to claim 3, wherein the diol is an aliphatic diol of formula II.

14. The process according to claim 1, wherein the reacting is carried out in the presence of a catalyst, which catalyst is an alkali metal alkoxide of the diol, and the diol is partly converted by addition of sodium hydroxide or potassium hydroxide in solid or aqueous form into the corresponding sodium or potassium alkoxide before the reaction with acetylene.

15. The process according to claim 14, wherein from 0.1 to 20 mol % of the hydroxy groups are converted into alkoxide groups.

16. The process according to claim 14, wherein from 0.5 to 10 mol % of the hydroxy groups are converted into alkoxide groups.

17. The process according to claim 1, wherein the extractive distillation of the product mixture is directly carried out without further work-up of the product mixture or without prior removal of by-products, catalysts or unreacted starting materials from the product mixture.

* * * * *